United States Patent [19]

Orths et al.

[11] 4,229,412

[45] Oct. 21, 1980

[54] APPARATUS FOR THE DETERMINATION OF BOND FORMS OF GASES

[75] Inventors: Kurt Orths; Roland Prumbaum, both of Ratingen; Peter Berger, Düsseldorf-Benrath, all of Fed. Rep. of Germany

[73] Assignee: Ströhlein GmbH & Co., Düsseldorf, Fed. Rep. of Germany

[21] Appl. No.: 969,004

[22] Filed: Dec. 13, 1978

[30] Foreign Application Priority Data

Dec. 14, 1977 [DE] Fed. Rep. of Germany ....... 2755587

[51] Int. Cl.³ ...................... G01N 31/12; G01N 33/20
[52] U.S. Cl. .................................. 422/80; 23/230 PC; 73/25; 422/78
[58] Field of Search ............... 23/230 PC; 422/78, 80; 73/25, 19

[56] References Cited

U.S. PATENT DOCUMENTS

| | | | |
|---|---|---|---|
| 3,279,888 | 10/1966 | Holler | 23/230 PC |
| 3,407,041 | 10/1968 | Kraus | 23/230 PC |
| 3,847,546 | 11/1974 | Paul | 23/230 PC |

Primary Examiner—R. E. Serwin
Attorney, Agent, or Firm—J. Harold Nissen

[57] ABSTRACT

Apparatus for the determination of bond forms of gases, such as a sample containing oxygen or nitrogen in solid or liquid small metal samples (e.g. from 0.8 to 1.2 g).

The apparatus includes a furnace to heat the sample to a temperature of about 3000° C. maximum in less than five minutes, a control device to control the rate at a value between 20° C./sec and 350° C./sec, a gas analyzer coupled to the furnace to indicate as a function of the supplied gas the quantities of gas released from the furnace in equal periods of time, and a computer coupled to the furnace and to the gas analyzer for receiving therefrom a measured value sequence in the form of a curve (Evologram) related to the gas quantities released per unit time to the computer for the determination of the bond forms of the gases contained in the sample, and the computer forms a first derivative curve and a second derivative curve from the measured value curve (Evologram) to form measured values between successive points in a minimum position and/or points which occur as a second inflection point immediately after a first inflection point on the measured value curve, these point positions being identified by zero indications and extreme positions on the derivative curves.

7 Claims, 3 Drawing Figures

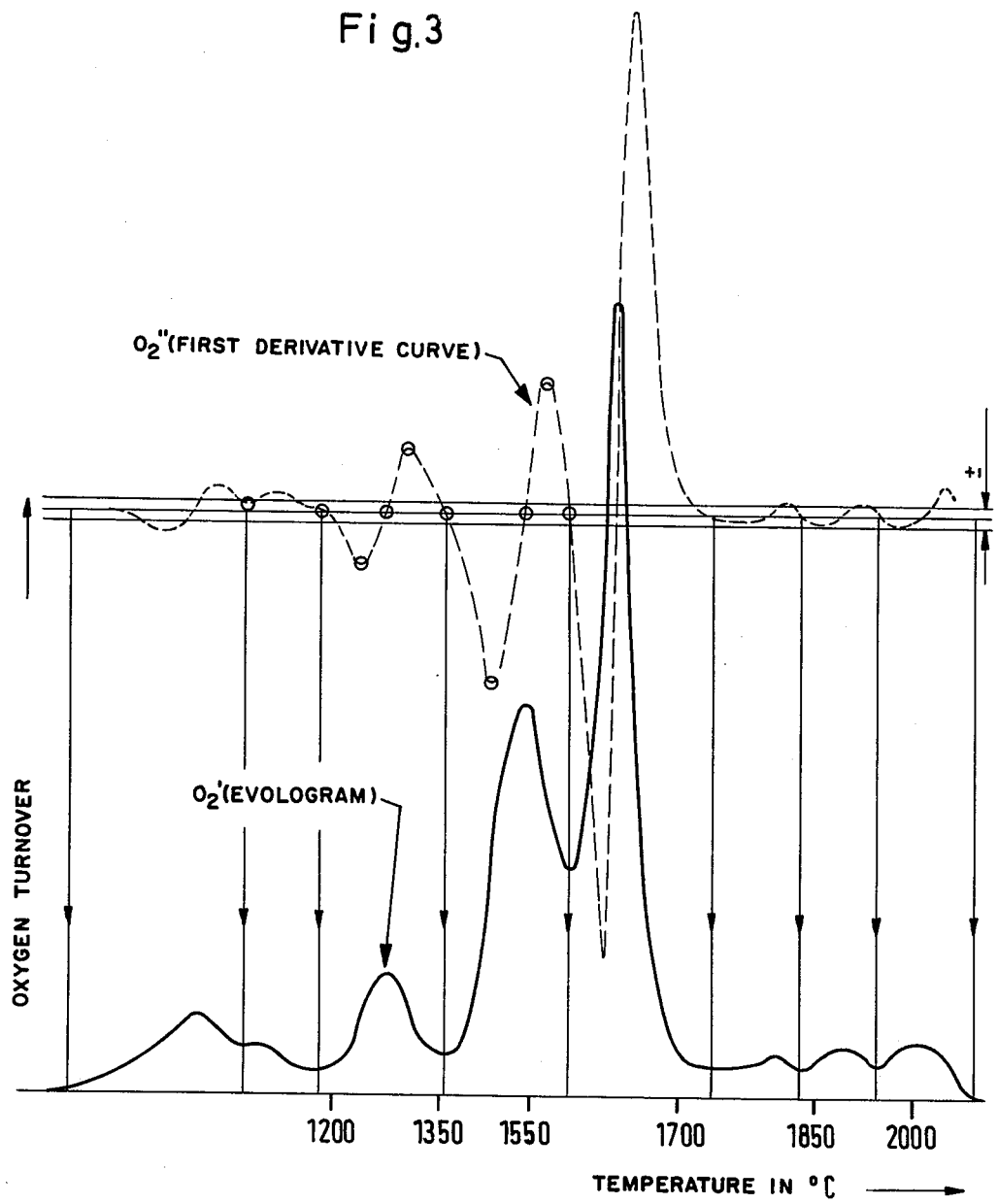

APPARATUS FOR THE DETERMINATION OF BOND FORMS OF GASES

BACKGROUND OF THE INVENTION

1. Field of the Invention

This invention relates to apparatus for quantitatively determining the total gas released from gas containing compounds and their bond forms.

More particularly, the invention relates to apparatus for determining the bond form of oxygen or nitrogen in solid or liquid small metal samples at a more rapid rate than heretofore possible, in addition to the quantity of oxygen or nitrogen in oxygen or nitrogen containing compounds, respectively.

DESCRIPTION OF THE PRIOR ART

In the metallurgical field, it is necessary to evaluate iron-carbon alloys. Not only is it necessary to know the total oxygen contents and the total nitrogen contents, it is also necessary to know the bond forms of these elements as well as their contents in melts or castings.

For many years, identification and determination of different oxide and nitride types was left to the analysis or residues and to metallography. While metallographic examination furnishes only semiquantitative results, a disadvantage of residue analysis is that it is very time-consuming.

A faster method of determining the oxides and nitrides is by so-called hot extraction method, in which the quantity of oxygen extracted and the respective reaction velocity are plotted over the temperature. To be able to treat this curve (Evologram) analytically according to the various bond forms, e.g. of oxygen, one must operate with a heating rate of say 10° C./min. This means that raising the temperature to about 2000° C. alone still takes several hours. But it takes even longer to separate the test curve into distinguishable collectives for different bond forms of the gases according to the classic method of Deaves and Beckel which is carried out by hand.

It is an object of the invention to provide apparatus for the rapid determination of gases, such as oxygen or nitrogen or their bond forms in solid or liquid small metal samples by means of which the various bond forms can be determined substantially faster than before.

The point of departure of the invention is apparatus or equipment for the rapid determination of the bond forms of gases, such as oxygen or nitrogen, in solid or liquid small metal samples (e.g. of 0.5–2 g, preferably 0.8–1.2 g). The apparatus includes: a furnace in which a sample, in particular one contained in a graphite crucible, is heated to a temperature of about 3000° C. maximum in less than five minutes; and, a gas analyzer to which the gas released during heating in the furnace is supplied continuously and which indicates the quantity of gas released in equal periods of time as a function of gas supplied to it.

In such an apparatus according to the invention, a furnace is provided which comprises a control device which, at a sample temperature above 1000° C. keeps the heating velocity of the sample constant at a value between 20° C./sec and 350° C./sec, and preferably between 50° and 180° C./sec. The gas analyzer furnishes a measured value sequence for the quantity of gas released per unit time to a computer. In order to determine the bond forms of the gases contained in the sample, after formation of the first and second derivatives of the measured value curve (Evologram) which corresponds to the entered measured value sequence, the computer forms the subtotals on collectives of these measured values between successive points in minimum position and/or points which occur as a second turning point (or inflection point) immediately after a first turning point (first inflection point) on the measured value curve (Evologram or oxide spectrum). These positions (minima, second turning point after the first turning point) are identified from the first and second derivatives of the measured value curve by zero indications and extreme positions.

With such an equipment, the gases are determined as to their bond forms in a very short time, about 3 minutes. While in the classic method, the Evologram according to Deavens and Beckel is segregated into single collectives to be able to determine the bond forms with great accuracy, in accordance with the invention the Evologram is cut at certain points and the measured values lying therebetween are summed or added up.

This considerable simplification, which at the same time comprises a complete objectivation of the method of evaluation with the possibility of digital indication of quantities of certain oxide or inclusion types, has been compared with the earlier method of evaluation by regression calculation. With a degree of definition $B=95\%$ and a residual scatter of $s=2.1$ ppm, the static certainty of this relationship is $\geq 99\%$; hence this finding can be used as a calibration curve.

As it is very important for the accuracy of the measured results supplied by the equipment that the furnace must heat the sample by equal amounts in equal periods of time, the control device must respond to temperature changes of the sample as smoothly as possible. For this purpose, a sensor is preferably used as an actual value transmitter of the control device which picks up the sample temperature without contact. This sensor can pick up the sample temperature with a photoconductor designed as a quartz rod. Such a sensor may be inserted in the wall of the sample vessel and terminate by its end face with the inside of the vessel, or, in the case of a graphite crucible of a resistance furnace, be arranged in front of the wall of the crucible.

With the device according to the invention it is possible not only, as before to determine quantitatively the total oxygen released, but at the same time, it is also possible to correlate the oxygen quantitatively to the various bond forms in a very short time. As this determination occurs in periods of less than 3 minutes, it is possible for the first time to give the steel mill man and caster control possibilities during the various melting operations, such as blowing, fining, deoxidizing, denitriding or also inoculating. In practice, certain oxides or nitrides present in the melt may lead to casting defects, such as heat cracks, gas bubbles and conchoidal fracture, which noticeably impair the technological properties of iron and steel. The equipment according to the invention for the first time provides information important for melt technology and deoxidation so quickly that with it the process can be modified in good time. Therefore, the purity of the melt is improved, and the inoculation of casting alloys can be evaluated objectively and kept under control qualitatively.

The equipment of the invention is especially suitable also for foundries, e.g. in the production of cast iron with lamellar graphite or spherical graphite as well as chill cast iron or malleable cast iron.

Other objects, advantages and the nature of the invention will become readily apparent from the detailed description of the invention described in connection with the accompanying drawings.

BRIEF DESCRIPTION OF THE DRAWINGS

FIG. 3 is a graphical representation of the measured value curve (Evologram) recorded by the computer which forms one of the units of the apparatus of FIG. 1, shown in full outline. And, the first derivative of the measured value curve is shown in dashed outline.

DESCRIPTION OF THE PREFERRED EMBODIMENTS

Figure 2:
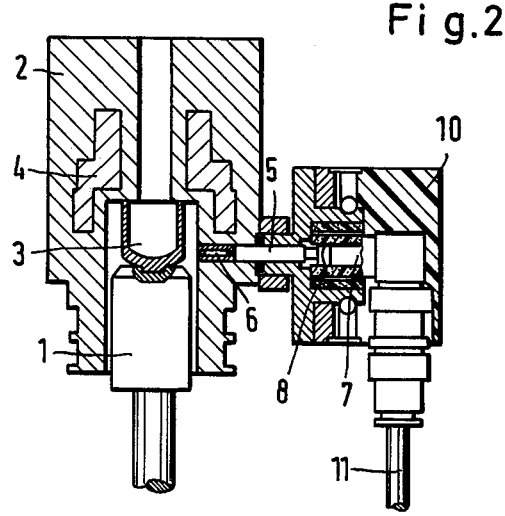
FIG. 2 is an axial section of a furnace and a sensor device forming two of the units of the apparatus of FIG. 1. The furnace is shown with a graphite crucible and the sensor device adapted to sense the temperature of the furnace.

Referring to the drawings which illustrates the preferred apparatus according to the invention and the system for determining the bond form of a gas, such as oxygen (e.g. oxygen in the form of FeO, MnO, $SiO_2$, $TiO_2$ or $Al_2O_3$), reference is made in particular to FIG. 2 which illustrates a graphite resistance furnace in which a 1 g sample of a steel or cast iron alloy is heated. The furnace comprises a lower electrode 1, an upper electrode 2 and a graphite crucible 3 arranged therebetween for receiving the 1 g sample. An annular channel for water cooling is provided in the upper electrode 2. A quartz rod 4 is mounted in a radial bore of the upper electrode 2, in the region of the graphite crucible 3. A shutter 5 is arranged in front of the quartz rod 4 so that the radiation from the graphite crucible impinging onto shutter 5 is only partially transmitted by the quartz rod 4.

A temperature sensor, which forms part of a sensor device is coupled with a photo-transistor 7 and is mounted in an insulated bushing 8 in a housing 10 which is fastened to the upper electrode 2. Photo-resistor 7 supplies a signal to an output line 11; this signal corresponds to the intensity of the radiation of the graphite crucible 3, and hence also to the temperature of the sample. The sensor device terminates by its end face 6 with the inside of the sample vessel or in front of the wall of the graphite crucible 3.

Figure 1:
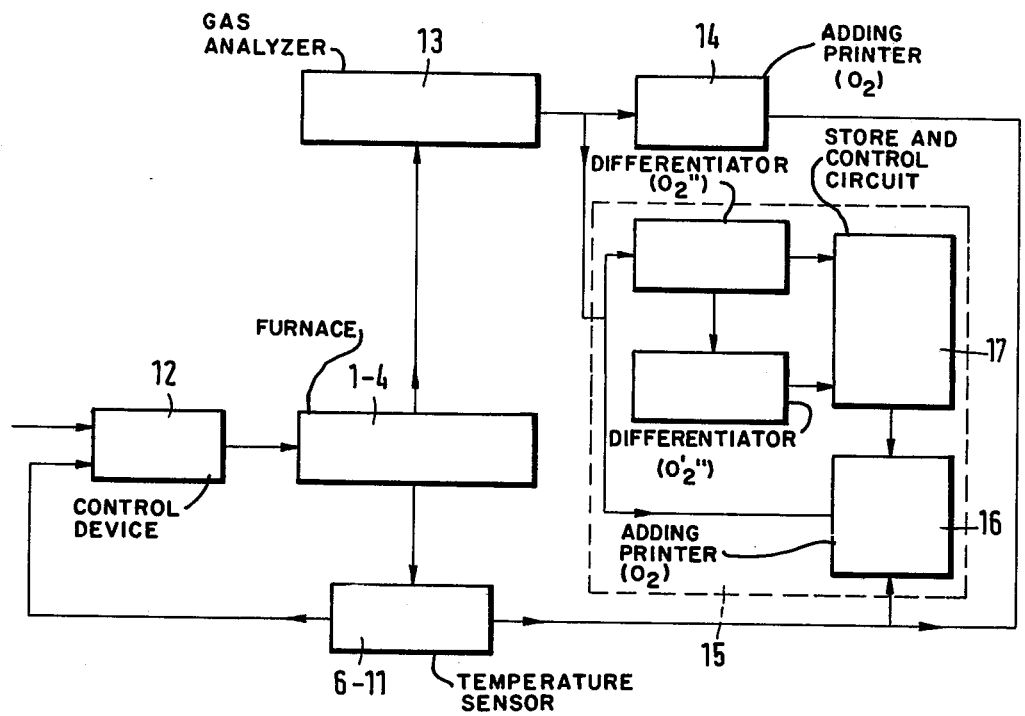
FIG. 1 is a block diagram schematically illustrating the interconnection of the units forming the apparatus of the invention.

Referring now more particularly to FIG. 1, the apparatus includes a control device or regulator 12 for regulating the current supply to the resistance furnace 1-4.

Coupled with the control device is the output from the sensor device 6-11 (6, 7, 8, 10, 11). The output from the control device is coupled with the furnace 1-4 (1, 2, 3, 4). The output of the furnace is connected with a gas analyzer 13. A computer 15 is coupled to the output of the sensor device 6-11 and the gas analyzer 13. An adding printer 14 is provided which is responsive to the outputs of gas analyzer 13 and sensor device 6-11. The computer 15 includes a printer 16 which is coupled with a control device 17. Control device 17 issues stop-start signals to the printer for controlling the operation thereof.

In FIG. 3, two curves on a single plot are shown with the abscissa being the temperature in degrees °C., and the ordinate being the gas, in this case oxygen.

As a set value, the regulator 12 receives the temperature linearly rising over time at a value of 20 to 350° C./sec, and more particularly or specifically 70° to 120° C./sec. By means of the aforedescribed temperature sensor 6-11, it is possible to control, practically inertialessly, this rapid heating of the small sample from about 700° C. to the desired end temperature (i.e. to 3000° C. max.). The CO gases released during this heating are picked up by the analyzer 13 and recorded by the adding printer 14, possibly over the temperature response. Moreover, the measured values furnished by the analyzer 13 are supplied to the computer 15. The printer 16 does not progressively total the oxygen released as CO gas of the different oxide compounds, but it receives the Stop-Start signals from the control device 17, so that in certain equal periods of time, the individual released gas quantities are added up. This may be effected over the temperature response in the same manner as in the printer 14.

The Stop-Start signals for the printer 16 are generated as a function of the measured valve or measurement curve (Evologram) furnished by the analyzer 13. To this end there are formed in computer 15 the first derivative curve ($O_2''$) and the second derivative curve ($O_2'''$) from the measured value curve ($O_2'$=Evologram=first derivative of the conversion curve) of the analyzer 13 in the computer 15. In FIG. 3, the measured value curve ($O_2'$) furnished by analyzer 13 and the first derivative thereof ($O_2''$) are shown one above the other, while the second derivative thereof ($O_2'''$) is not shown. The control device 17 checks with reference to these data ($O_2''$ and $O_2'''$) the measured value curve ($O_2'$) of the analyzer 13 for open and concealed minima and sends a Stop/Start signal to the printer 16 at each minimum. The Stop/Start signal is issued at which the measured values totaled up to this moment are printed out, and the measured values furnished thereafter are totaled anew. While each open minimum of the measured value curve ($O_2'$) is exactly identifiable in connection with a zero crossing of the differentiated measured value curve ($O_2''$), the signal for a concealed minimum is obtained by approximation, by the second of two successive turning points of the measured value curve ($O_2'$), and it is identified exactly from the data of the first and second derivatives of the measured value curve ($O_2''$ and $O_2'''$).

In FIG. 3, arrow lines are drawn down from curve ($O_2$ and $O_2''$), mark the points at which, as a function of the measured value curve differentiated once and twice, the control device 17 delivers the Stop/Start signal to the printer 16.

While the example was explained with reference to the oxygen compounds, the invention can be equally applied correspondingly to nitrogen compounds. The equipment remains the same, only one must determine the released nitrogen quantity.

We claim:

1. Apparatus for the determination of bond forms of gases, such as a sample containing oxygen or nitrogen in solid or liquid small metal samples e.g. from 0.8 to 1.2 g comprising:

a furnace for heating the sample continuously to elevate the temperature thereof to a temperature of about 3000° C. maximum in less than five minutes to release gases from the sample, said furnace comprising a control device for presetting a constant heating rate of the sample for the constant heating thereof at a value between 20° C./sec and 350° C./sec, a gas analyzer operatively coupled to said furnace from which the gas released during heating is supplied continuously for picking up the gas released during heating by said furnace, said gas analyzer indicating as a function of this supplied gas the quantities of the gas released in equal periods of time, and a computer operatively coupled to said furnace and to said gas analyzer, said gas analyzer providing as an output, a measured value sequence in the form of an oxide spectrum curve or Evologram characteristic thereof for the gas quantities released per unit time to said computer for the determination of the bond forms of the gases contained in the sample, said computer detecting the desired values from the characteristic curve and forming a first derivative curve and a second derivative curve from the said measured value curve or Evologram corresponding to the entered measured value sequence, for forming subtotals of these measured values between successive points in a minimum position and/or points which occur as a second inflection point immediately after a first inflection point on the measured value curve or, these positions, minima, inflection point after inflection point being identified from the first and second derivatives of the measured value curve by zero indications and extreme positions.

2. Apparatus according to claim 1, including:
a sensor coupled with said control device and said furnace for picking up the temperature of the sample without contact.

3. Apparatus according to claim 2, wherein said sensor device quartz rod for picking up the sample temperature.

4. Apparatus according to claim 2 or 3, wherein said furnace includes a sample vessel having a wall, and said sensor device has an end face inserted into said wall and terminating inside said sample vessel.

5. Apparatus according to claim 2 or 3, wherein said furnace includes a graphite crucible and said sensor device is operatively associated with said graphite crucible to supply an output corresponding to the intensity of radiation of the graphite crucible and the temperature of the sample.

6. Apparatus according to claim 5, wherein said sensor device is arranged in front of the wall of said graphite crucible.

7. Apparatus according to claim 1 wherein said sensor device includes a quartz rod operatively associated with said furnace to sense the temperature characteristic thereof.

* * * * *